(12) United States Patent
Beebe et al.

(10) Patent No.: US 7,470,403 B2
(45) Date of Patent: Dec. 30, 2008

(54) MICROFLUIDIC PLATFORM AND METHOD OF GENERATING A GRADIENT THEREIN

(75) Inventors: David J. Beebe, Monona, WI (US); Vinay V. Abhyankar, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 156 days.

(21) Appl. No.: 11/411,671

(22) Filed: Apr. 26, 2006

(65) Prior Publication Data
US 2007/0253868 A1 Nov. 1, 2007

(51) Int. Cl.
*B01L 3/02* (2006.01)
(52) U.S. Cl. ...................................... 422/100
(58) Field of Classification Search ............ 422/100
See application file for complete search history.

(56) References Cited

U.S. PATENT DOCUMENTS 6,695,765 B1 * 2/2004 Beebe et al. .............. 600/33

OTHER PUBLICATIONS

Lim, J.M.; Reggio, B.C.; Godke, R.A.; Hansel, W. "A Continuous flow, perfusion culture system for 8- to 16-cell bovine embryos derived from in vitro culture." Theriogenology. 1996, vol. 46, 1441-1450.*

Presentation, University of Wisconsin, Madison, WI, Apr. 6, 2005, entitled "Using Surface Patterning And Microfluidics to Understand Human Embryonic Stem Cell Differentiation" by Abhyankar et al.

Paper from the Journal of *The Royal Society Of Chemistry*, dated Apr. 22, 2005, entitled "Effects of flow and diffusion on chemotaxis studies in a microfabricated gradient generator" by Walker et al.

Article from *Langmuir* 2000, pp. 8311-8316, entitled: "Generation of Solution and Surface Gradients Using Microfluidic Systems" by Jeon et al.

Report from *Science* vol. 287, dated Feb. 11, 2000, entitled "Polarization Of Chemoattractant Receptor Signaling During Neutrophil Chemotaxis" by Servant et al.

* cited by examiner

*Primary Examiner*—Walter D Griffin
*Assistant Examiner*—Bobby Ramdhanie
(74) *Attorney, Agent, or Firm*—Boyle Fredrickson, S.C.

(57) ABSTRACT

An apparatus and method of using the same are provided for generating a gradient of particles within a microfluidic device. The microfluidic device includes a channel having an input and an output. The channel is filled with a predetermined fluid. Thereafter, particles from a source pass through a porous membrane into the input of the channel. A second membrane is provided adjacent the output of the channel to minimize convection therein. A sink communicates with the output of the channel. The source/sink combination creates a pseudo-steady state in the channel wherein the concentration of particles at a point does not vary dramatically with time.

12 Claims, 4 Drawing Sheets

MICROFLUIDIC PLATFORM AND METHOD OF GENERATING A GRADIENT THEREIN

REFERENCE TO GOVERNMENT GRANT

This invention was made with United States government support awarded by the following agencies: NIH HL072089. The United States has certain rights in this invention.

FIELD OF THE INVENTION

This invention relates generally to microfluidic devices, and in particular, to a microfluidic platform and a method of generating a gradient therein.

BACKGROUND AND SUMMARY OF THE INVENTION

Chemical gradients play an important role in mediating biological activity in vivo. Insight into the interplay between a chemical gradient treatment and the corresponding cellular response may help to determine the cues that trigger changes in gene expression that are responsible for regulating specific cellular activities. Understanding the importance of these chemical cues could help researchers develop controlled microenvironments wherein the desired cellular response is produced by combining the effects of exogenous controlled gradient treatments with ongoing endogeneous cell-cell signaling.

Prior to the development of laminar flow based gradient generators, it was difficult to accurately develop and predict the chemical microenvironment to which cells are exposed. Laminar flow based gradient generators create chemical gradients by taking advantage of diffusional mixing across the interface of adjacently flowing streams. With these gradient generators, it is possible to treat a cell population with a controlled chemical gradient and to observe the biochemical and morphological responses of the cell in vitro.

These prior gradient generators include continuously flowing streams of fluid that provide precise control over the stability, gradient profile, concentration range and slope of a chemical gradient. The stimulus of interest can be changed "on the fly" to create a sequential chemical gradient treatment scheme. Flow based gradient generators have been used to successfully study neutrophil chemotaxis and neuronal differentiation in vitro. While these gradient generators are robust and provide excellent control over the chemical gradient characteristics, the continuously flowing streams that are necessary to maintain chemical gradients make these devices unsuitable for addressing certain biological questions wherein soluble factors are important in regulating cell behavior.

One way that cells respond to chemical cues in their environment is by secreting signaling factors that either affect the secreting cell itself (autocrine), or affect other types of cells (paracrine). In flow based gradient generators, autocrine/paracrine factors of a cell cannot accumulate because the flowing fluid streams immediately carry the secreted factors away. In situations where cell-cell communication (via soluble factors) plays a critical role in regulating biochemical activity, the removal or accumulation of secreted factors may lead to distinctly different cellular behavior. In view of the foregoing, it can be appreciated that to provide a microfluidic gradient generator that does not require flowing fluid streams to develop a stable chemical gradient.

Therefore, it is a primary object and feature of the present invention to provide a microfluidic platform and a method of generating a gradient therein.

It is a further object and feature of the present invention to a microfluidic platform and a method of generating a gradient therein that does not require flowing fluid streams to develop a gradient.

It is a still further object and feature of the present invention to a microfluidic platform and a method of generating a gradient therein that allows for the introduction of media into the gradient without generating convection.

It is a still further object and feature of the present invention to provide a microfluidic platform and a method of generating a gradient therein that is simple to utilize and inexpensive to manufacture.

In accordance with the present invention, a microfluidic device is provided for generating a gradient. The microfluidic device includes a body defining a source and a gradient channel. The gradient channel has an input port and an output. A first membrane separates the input port of the gradient channel and the source. A second membrane is disposed downstream of the first membrane. A sink communicates with the output of the gradient channel.

The sink may include a flow channel extending through the body and the second membrane may be disposed adjacent the output of the gradient channel. Alternatively, the sink may include a chamber having a predetermined volume. The gradient channel has a predetermined volume that is less than the predetermined volume of the sink. A media addition port communicating with the sink may also be provided in the body. The second membrane may be disposed across the media addition port. It is contemplated for the membranes to be formed from a polycarbonate material.

In accordance with a further aspect of the present invention, a microfluidic device is provided for generating a gradient. The microfluidic device includes a body and a first membrane. The body defines a source channel extending along a first axis and having an output; a gradient channel at a predetermined angle to the source channel; and a sink communicating with the output of the gradient channel. The sink is defined by a flow channel extending through the body. The gradient channel includes an input communicating with the output of the source channel and an output. The first membrane extends through the source channel.

The gradient channel extends along a second axis that is generally perpendicular to the first axis. The sink may include a flow channel extending through the body or a chamber having a predetermined volume. The gradient channel has a predetermined volume that is less than the predetermined volume of the chamber of the sink. It is contemplated for the source channel to have an input operatively connected to a source of particles. The input of the source channel lies in a first plane and the gradient channel lies in a second plane axially spaced from the first plane.

In accordance with a still further aspect of the present invention, a method is provided for generating a gradient of particles within a microfluidic device. The microfluidic device defines a channel having an input and an output. The method includes the steps of filling the channel with a predetermined fluid and passing the particles through a porous first membrane into the channel. A second membrane is provided downstream of the first membrane to limit convection of the fluid in the channel.

A sink may be provided at the output of the channel. The sink includes a generally constant concentration of particles therein. The channel has a predetermined volume that is less than a predetermined volume of the sink. It is contemplated for a fluid stream to communicate with the sink. The method also contemplates passing the particles through a second porous membrane into the channel.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings.

DETAILED DESCRIPTION OF THE DRAWINGS

Figure 1:
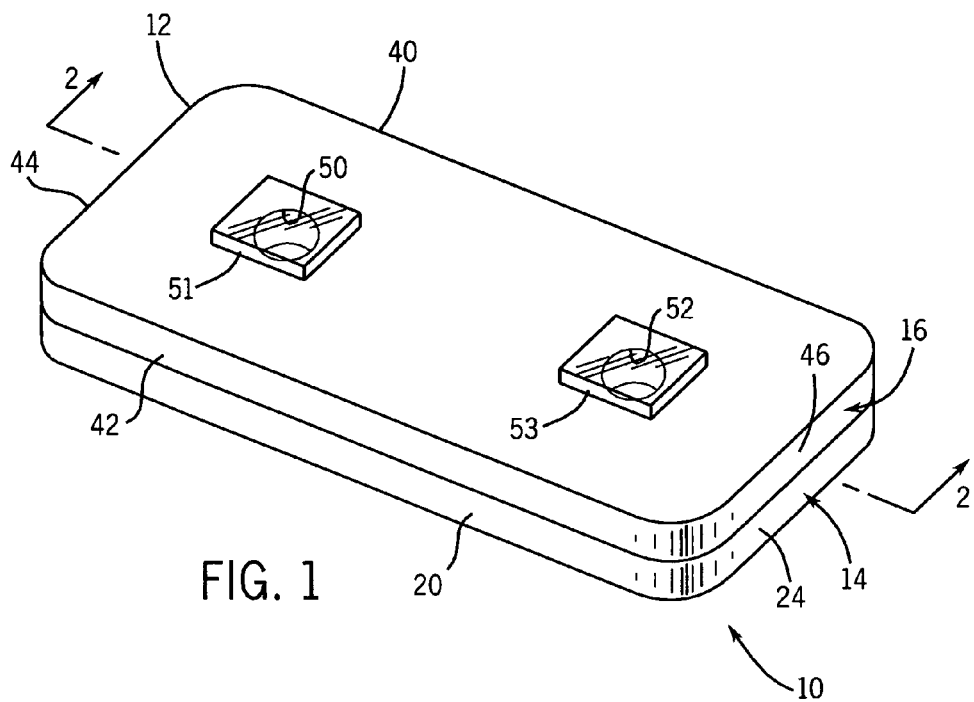
FIG. 1 is an isometric view of a microfluidic device for performing a methodology in accordance with the present invention.
Figure 2:
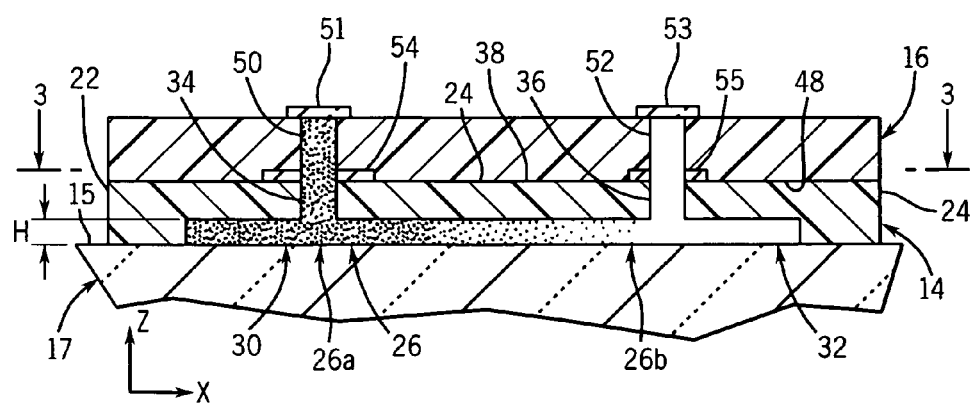
FIG. 2 is a cross sectional view of the microfluidic device taken along line 2-2 of FIG. 1.
Figure 3:
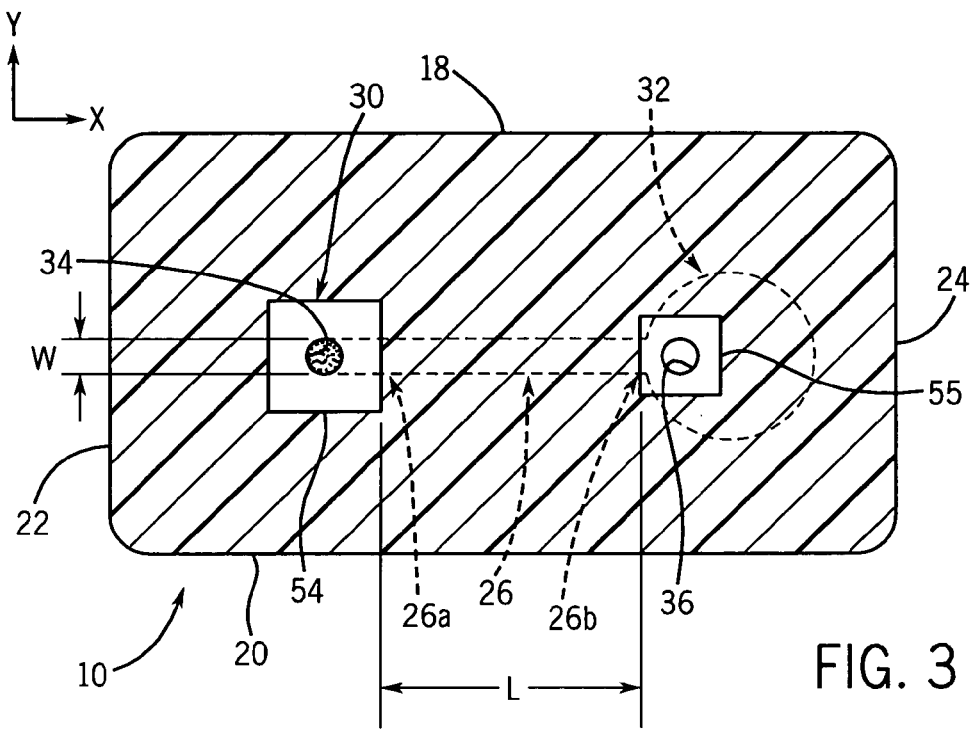
FIG. 3 is a cross sectional view of the microfluidic device taken along line 3-3 of FIG. 2.

Referring to FIGS. 1-3, the present invention includes a microfluidic device generally designated by the reference numeral 10 that performs the methodology of the present invention. It can be appreciated that microfluidic device 10 can have various configurations without deviating from the scope of the present invention. In the contemplated embodiment, microfluidic device 10 is fabricated from (poly)dimethylsiloxane (PDMS) using soft lithography and rapid prototyping. However, microfluidic device may be fabricated from other materials using other manufacturing techniques.

Microfluidic device 10 includes bottom channel layer 14 and top fluid reservoir layer 16. Bottom channel layer 14 positioned on upper surface 15 of microscope slide 17 or other similar substrate, such as a silicon wafer or print circuited board, without deviating from the scope of the present invention. In the depicted embodiment, bottom channel layer 14 has a generally rectangular configuration and is defined by first and second sides 18 and 20, respectively, and first and second ends 22 and 24, respectively. Channel 26 is provided in lower surface 28 of bottom channel layer 14 and extends along a longitudinal axis between a source region 30 and an enlarged sink region 32. Access ports 34 and 36 are punched in upper surface 38 of bottom channel layer 14, respectively, with a sharpened coring tool. It is intended for access port 34 to communicate with source region 30 and for access port 36 to communicate with sink region 32. For reasons hereinafter described, sink region 32 in lower surface 28 of bottom channel layer 14 has a diameter greater than the diameter of source region 30.

Similar to bottom channel layer 14, top fluid reservoir layer 16 has a generally rectangular configuration and is defined by first and second sides 40 and 42, respectively, and first and second ends 44 and 46, respectively. Access ports 50 and 52 are punched through top fluid reservoir layer 16 with a sharpened coring tool.

In order to assemble microfluidic device 10, access port 34 of the bottom channel layer 14 is covered with membrane 54 having pores therethrough of a predetermined diameter (e.g., 0.2 micrometers). Thereafter, lower surface 48 of top fluid reservoir layer 16 is positioned on upper surface 38 of bottom channel layer 14 such that first and second sides 40 and 42, respectively, of top fluid reservoir layer 16 are aligned with first and second sides 18 and 20, respectively, of bottom channel layer 14 and such that first and second ends 44 and 46, respectively, of top fluid reservoir layer 16 are aligned with first and second ends 22 and 24, respectively, of bottom channel layer 14. Bottom channel layer 14 and top fluid reservoir layer 16 are permanently bonded together using oxygen plasma treatment. With microfluidic device 10 assembled, membrane 54 is sandwiched in between bottom channel layer 14 and top fluid reservoir layer 16 and provides a porous barrier between access port 50 through top fluid reservoir layer 16 and access port 34 in bottom channel layer 14. Second membrane 55 is also sandwiched in between bottom channel layer 14 and top fluid reservoir layer 16 and provides a porous barrier between access port 52 through top fluid reservoir layer 16 and access port 36 in bottom channel layer 14.

In operation, access ports 34 and 36 in bottom channel layer 14; access ports 50 and 52 in top fluid reservoir layer 16; channel 26 in bottom channel layer 14; source region 30 in bottom channel layer 14 and sink region in bottom channel layer 14 are filled with a first predetermined solution, such as deionized water. A predetermined fluid having a known concentration of particles, such as cells, molecules, chemical species, organisms or the like, therein are introduced or loaded into microfluidic device 10 through access port 50 in top fluid reservoir layer 16. Glass cover slips 51 and 53 are placed on upper surface 49 of top fluid reservoir layer 16 so as to overlap and seal corresponding access ports 50 and 52, respectively, to prevent evaporation of the predetermined fluid.

For reasons hereinafter described, diffusive transport of the predetermined fluid is allowed through membrane 54 while the fluidic resistance of membrane 54 minimizes the convective flows in channel 26. As a result, the predetermined fluid diffuses through membrane 54 and into channel 26 creating a concentration gradient of particles from source region 30 to sink region 32 over a predetermined time period (also hereinafter referred to as the "gradient development period").

It can be appreciated that a mathematical model may be used to guide design of the various aspects of microfluidic device 10. More specifically, the volumetric flow rate is proportional to the pressure gradient along the fluid path and inversely proportional to the fluidic resistance.

$$Q = \frac{\Delta P}{R} \qquad \text{Equation (1)}$$

wherein Q is the volumetric flow rate; $\Delta P$ is the pressure gradient along a fluid path; and R is the fluidic resistance.

Referring to Equation (1), it is possible to limit flow rate by ensuring that the fluid levels at inlet end 26a and at outlet end 26b of channel 26 are equal ($\Delta P=0$). This approach is problematic for microfluidic systems because it is difficult to precisely match fluid levels. Surface tension effects can also lead to pressure differences that result in observable fluid flow. In order to limit fluid flow resulting from small pressure differences, porous membrane 54 having a high fluidic resistance is incorporated into microfluidic device 10. Membrane 54 helps limit fluid flow of the predetermined fluid in channel 26 due to any pressure imbalances by increasing the fluidic resistance of the system (as R increases, Q decreases). For small particles such as molecules in the predetermined fluid, the resistance of membrane 54 does not affect diffusive transport into the system.

As heretofore described, the particles in the predetermined fluid enter channel 26 by diffusing through membrane 54 in source region 30. After the predetermined time period, a concentration gradient is created along the length of channel 26. The source/sink concept is used to create a pseudo-steady state in channel 26 wherein the concentration at a point does not vary dramatically with time.

An ideal source/sink setup maintains constant concentrations in source region 30 and sink region 32 by providing an infinite source of particles at the source region and a sink region of infinite size. As hereinafter described, an ideal source/sink setup may be achieved by using flowing fluid steams to maintain the desired concentrations at source region 30 and sink region 32. Alternatively, referring to the embodiment of the present invention depicted in FIGS. 1-3, the ideal source/sink setup is achieved without using fluid flow by providing source and sink regions 30 and 32, respectively, with volumes that are much larger that the volume of channel 26. The large volume sink region 32 at output end 26b of channel 26 helps maintain the concentration gradient by not allowing the particles to accumulate in channel 26. Without a large volume reservoir such as sink region 32, the particles would accumulate in channel 26 and the concentration gradient in channel 26 would not reach a pseudo-steady state value.

A quantification or mass balance of particulate flowing into and out of channel 26 may be used to confirm that the gradient inside of channel 26 does not change as long as the change of concentration of particles entering channel 26 over the predetermined time period equals the change in particles leaving the channel 26 over the predetermined time period. Once the change of concentration of particles entering channel 26 equals the change in particles leaving the channel 26 over the predetermined time period, the system enters a pseudo-steady state where the gradient does not dramatically change over time. The finite period of time before the change in the concentration of particles entering channel 26 equals the change in the concentration of particles leaving the channel 26 is a function of the molecular diffusion coefficient and the length of channel 26. A simple numerical model (Equation 2) may be used to predict the duration of the gradient development period and model behavior of the system.

$$\frac{\partial c}{\partial t} = -D\nabla^2 c \qquad \text{(Equation 2)}$$

wherein $$\frac{\partial c}{\partial t}$$

is change in the concentration of particles in channel 26 over time; D is a molecular diffusion coefficient of member 54; c is the concentration of particles in channel 26; and $\nabla^2 c$ is the Laplacian operator ($\nabla \cdot (\nabla c)$) of the concentration of particles in channel 26 that describes the rate at which the concentration gradient ($\nabla c$) exits in a given region of space.

Figure 3A:
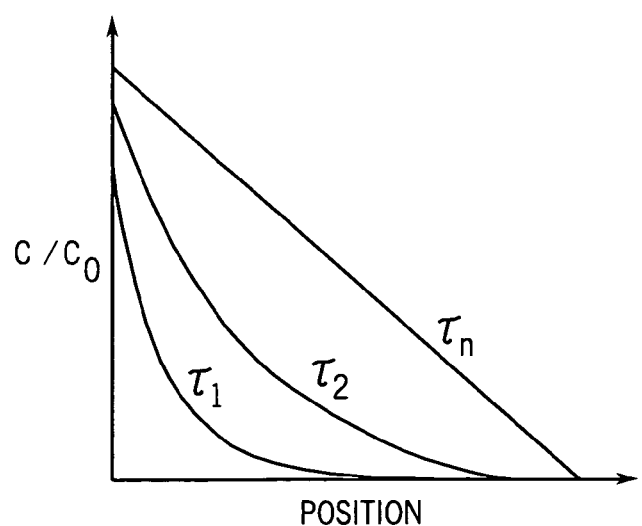
FIG. 3a is a graphical representation of the concentration gradients in the channel of the microfluidic device of the present invention at predetermined time periods versus the position along the channel.

As described, until reaching steady state, the concentration gradient is transient. FIG. 3a depicts the concentration gradients ($c/c_0$) in channel 26 at predetermined time periods $\tau_1$, $\tau_2$ and $\tau_n$ versus the position along channel 26 wherein $\tau_n$ represents the gradient development period. It can be appreciated that during the transient period, the concentration gradients have different slopes depending on the position along channel 26. For example, during the transient period, the slope of the concentration gradient is steeper at the beginning of channel 26 than at the end of channel 26.

The gradient within channel 26 in the z-direction, FIG. 2, can be neglected if the z-dimension is much smaller than the axial dimension (i.e., the height H of channel 26 is substantially smaller than the length L of channel 26). The gradient in the y-direction is neglected based on experimental observations. The solution to the diffusion equation of Equation 2 (with appropriate boundary conditions) provides information about the duration of the gradient development period and the pseudo-steady state concentration profile.

The initial and boundary conditions within microfluidic device 10 may be expressed as follows:

$$\frac{\partial c}{\partial t} = D\frac{\partial^2 c}{\partial x^2} \qquad \text{(Equation 3)}$$

wherein $$\frac{\partial c}{\partial t}$$

is change in the concentration of particles in channel 26 over time; D is the molecular diffusion coefficient of membrane 54;

$$\frac{\partial^2 c}{\partial x^2}$$

is the Laplacian operator of the concentration of particles in channel 26 in the x direction.

$$c(x,0)=0 \qquad \text{(Equation 4)}$$

wherein c(x,0) is the initial concentration of particles in channel 26.

$$\frac{\partial c(0,t)}{\partial x} = KA_m(c_0 - c) \qquad \text{(Equation 5)}$$

wherein $$\frac{\partial c(0,t)}{\partial x}$$

is the rate at which the particles enter channel 26; K is the partition coefficient of membrane 54; $A_m$ is the surface area of membrane 54; $c_0$ is the initial concentration of particles input into source region 30; and c is the concentration of particles in channel 26.

$$\frac{\partial c(L, t)}{\partial x} = -DA_c(c - c_\infty) \quad \text{(Equation 6)}$$

wherein $$\frac{\partial c(L, t)}{\partial x}$$

is the rate at which the particles leave channel 26; D is a molecular diffusion coefficient of member 54; $A_c$ is the cross-sectional area of channel 26; c is the concentration of particles in channel 26; and $c_\circ$ is the concentration of particles output at into sink region 32 from output end 26b of channel 26.

It can be appreciated that parameters of microfluidic device 10 can be easily changed to adjust the gradient development. The relative placement of the source and sink regions 30 and 32, respectively, determines the slope of the pseudo-steady state gradient. For example, increasing the axial distance between source region 30 and sink region 32 results in less steep slopes of the gradient at its pseudo-steady state. The mathematical model heretofore described may be used as a predictive tool, as well as, a method to guide system design.

The normalized concentration value ($c/c_0$) in the pseudo-steady state gradient is a function of the porosity (percent void volume) of membrane 54. Important design parameters when choosing membrane 54 for this application include the hydrophilicity (to ensure proper wetting), membrane thickness, low protein binding and pore size. It can be appreciated that membrane 54 may be fabricated any porous material such as PDMS, nylon, polyester, or the like.

The pseudo-steady state gradient found from experimental data is not completely constant over time because the concentration in sink region 32 is not maintained at exactly zero (because the sink is not perfectly mixed). From Equation (4) the rate of particles leaving channel 26 is proportional to the difference between the concentration of particles in channel 26 and the concentration of particles in sink region 32. As the diffusing particles leave channel 26, the concentration of particles in the portion of sink region 32 adjacent to channel 26 becomes non-zero and the rate at which the particles leave channel 26 changes slightly over time. However, comparison between the model and experimental data suggests that the approximation of zero sink concentration is valid because the small concentration of incoming particles is diluted by the large fluid volume of sink region 32. One way to mimic an ideal sink would be to periodically flush out, replace or mix the reservoir volume.

It is contemplated to add cells to channel 26 after the gradient stabilization in order to determine the effects of the gradient on the cells. The cells may be introduced through a cell addition port defined by access ports 36 and 52 in microfluidic device 10. Large pore diameter membrane 55 extends through the cell addition port wherein the pore size is greater than the cell size. Large pore membrane 55 provides fluidic resistance to allow cell loading within channel 26 with minimal disturbance to the pseudo-steady state gradient. Cell addition after the gradient development time ensures that the cells experience a known and stable gradient.

Further, it is thought that the slope of a gradient may influence the migration rate of cells in vivo. This concept can be quantitatively tested using microfluidic device 10 of the present invention by employing a multiple source construct where a plurality of source regions 30 are placed at different distances from sink region 32 (resulting in a different pseudo-steady state slope). Cells can be introduced into a central location (after the gradient stabilization period) and the cellular migration that occurs in response to the varying gradient slopes can be observed in parallel to determine a correlation between cell migration and gradient slope. Multiple types of chemoattractants can also be similarly investigated to determine preferential behavior in response to an array of chemoattractants. The mathematical models heretofore described are a valuable tool in the design of such experiments.

Figure 4:
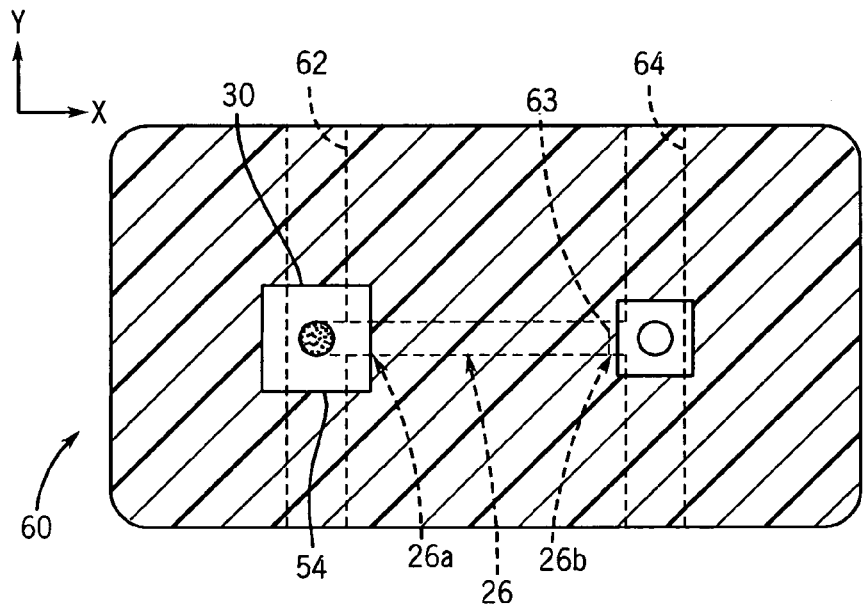
FIG. 4 is a cross sectional view, similar to FIG. 3, showing a second embodiment of a microfluidic device in accordance with the present invention.

Referring to FIG. 4, an alternate embodiment of the microfluidic device of the present invention is generally designated by the reference numeral 60. Microfluidic device 60 is similar to microfluidic device 10, and as such, the previous description of microfluidic device 10 is understood to describe microfluidic device 60 except as provided hereinafter.

In order to provide the ideal source/sink setup, flowing fluid steams may be used to maintain the desired concentrations of the particles at source region 30 and at output 26a of channel 26. Microfluidic device 60 includes first flow channel 62 extending through top fluid reservoir layer 16 and communicating with access port 34 in bottom channel layer 14 through membrane 54. Second flow channel 64 extends though bottom channel layer 14 and communicates with output 26a of channel 26.

In operation, first and second flow channels 62 and 64, respectively, as well as, channel 26 in bottom channel layer 14 are filled with a first predetermined solution, such as deionized water. A predetermined fluid having a known concentration of particles, such as cells, molecules, chemical species, organisms or the like, therein are introduced or loaded into microfluidic device 10 through first flow channel 62 in top fluid reservoir layer 16.

As heretofore described, diffusive transport of the predetermined fluid is allowed through membrane 54 while the fluidic resistance of membrane 54 minimizes the convective flows in channel 26. As a result, the particles in the predetermined fluid flowing through first flow channel 62 diffuse through membrane 54 and into channel 26 creating a concentration gradient of particles from source region 30 to output 26a thereof over a predetermined time period. The predetermined solution flows continuously through second flow channel 64 so as to maintain the concentration gradient by not allowing the particles to accumulate in channel 26. Once the change of concentration of particles entering channel 26 equals the change in particles leaving the channel 26 over the predetermined time period, the system enters a pseudo-steady state wherein the gradient does not dramatically change over time. It is contemplated to provided membrane 63 over the output end 26b of channel 26 to limit the convection in channel 26 resulting from the flow of fluid through first flow channel 62.

As described, the system of the present invention utilizes small volumes of particulate in source region 30. Further, the particulate is easily introduced into the system by placing a predetermined fluid having the particles over membrane 54 in source region 30 and allowing the particles to diffuse through membrane 54 and into channel 26.

As described, microfluidic devices 10 and 60, as well as, the method of the present invention provide a simple vehicle for creating a stable linear gradient using small stimulant volumes. The devices and method require no external equipment, and can be easily incorporated into existing biological studies. Microfluidic devices 10 and 60 are easy to fabricate and the designs of the microfluidic devices 10 and 60 can be easily modified to produce desired gradient characteristics.

Figure 5:
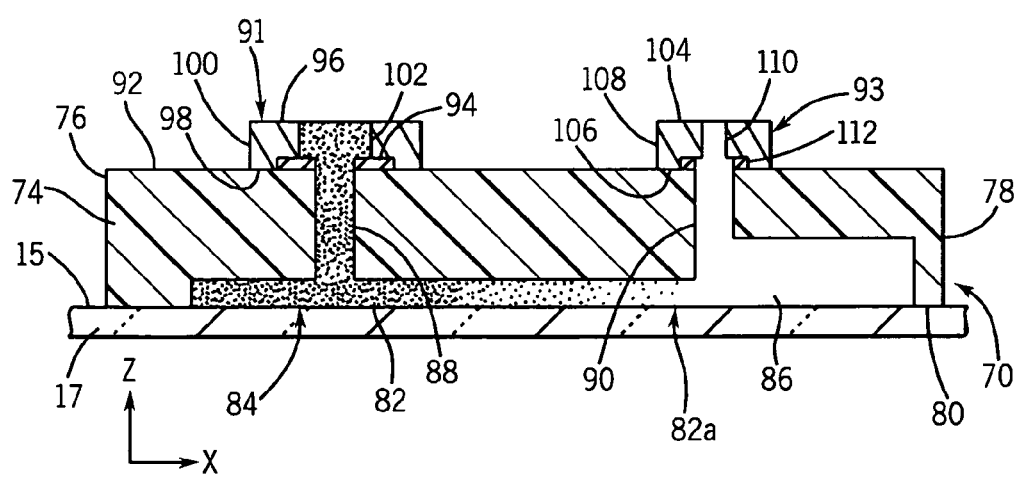
FIG. 5 is a cross sectional view of a third embodiment of a microfluidic device in accordance with the present invention.

Referring to FIG. 5, a third embodiment of the microfluidic device of the present invention is generally designated by the reference numeral 70. It can be appreciated that microfluidic device 70 can have various configurations without deviating from the scope of the present invention. In the contemplated embodiment, microfluidic device 70 is fabricated from (poly) dimethylsiloxane (PDMS) using soft lithography and rapid prototyping. However, microfluidic device may be fabricated from other materials using other manufacturing techniques.

Microfluidic device 70 includes channel layer 74 that is positionable on upper surface 15 of microscope slide 17 or other similar substrate, such as a silicon wafer or print circuited board, without deviating from the scope of the present invention. In the depicted embodiment, channel layer 74 has a generally rectangular configuration and is defined by first and second sides, and first and second ends 76 and 78, respectively. Channel 82 is provided in lower surface 80 of channel layer 74 and extends along a longitudinal axis between a source region 84 and an enlarged sink region 86. Access ports 88 and 90 are punched in upper surface 92 of channel layer 74 with a sharpened coring tool. It is intended for access port 88 to communicate with source region 84 and for access port 90 to communicate with sink region 86. For reasons hereinafter described, sink region 84 in lower surface 80 of channel layer 74 has a volume greater than the diameter of source region 86.

Microfluidic device 70 further includes removable source and cell-addition members 91 and 93, respectively. Source member 91 includes upper and lower surfaces 96 and 98, respectively, interconnected by outer periphery 100. Access port 102 is punched source member 91 with a sharpened coring tool. Cell-addition member 93 includes upper and lower surfaces 104 and 106, respectively, interconnected by outer periphery 108. Access port 110 is punched cell-addition member 93 with a sharpened coring tool.

In order to assemble microfluidic device 70, access port 88 of channel layer 74 is covered with membrane 94 having pores therethrough of a predetermined diameter (e.g., 0.2 micrometers). Thereafter, lower surface 98 of source member 91 is positioned on upper surface 92 of channel layer 74 such that access port 102 is axially aligned with access port 88. An adhesive may used to affix lower surface 98 of source member 91 to upper surface 92 of channel layer 74. As described, membrane 94 is sandwiched in between channel layer 74 and source member 91 and provides a porous barrier between access port 102 through source member 91 and access port 88 in channel layer 74. In addition, access port 90 of channel layer 74 is covered with membrane 112 having pores therethrough of a predetermined diameter (e.g., 0.2 micrometers). Thereafter, lower surface 106 of cell-addition member 93 is positioned on upper surface 92 of channel layer 74 such that access port 110 is axially aligned with access port 90. An adhesive may used to affix lower surface 98 of cell-addition member 93 to upper surface 92 of channel layer 74. As described, membrane 112 is sandwiched in between channel layer 74 and cell-addition member 93 and provides a porous barrier between access port 110 through cell-addition member 93 and access port 90 in channel layer 74.

In operation, access ports 88 and 90 in channel layer 74; access ports 102 and 110 in source and cell-addition members 91 and 93, respectively; channel 82 in channel layer 74; source region 840 in channel layer 74; and sink region 86 in channel layer 74 are filled with a first predetermined solution, such as deionized water. A predetermined fluid having a known concentration of particles, such as cells, molecules, chemical species, organisms or the like, therein are introduced or loaded into microfluidic device 70 through access port 102 in source member 91.

As heretofore described, diffusive transport of the predetermined fluid is allowed through membrane 94 while the fluidic resistance of membrane 94 minimizes the convective flows in channel 82. As a result, the particles in the predetermined fluid diffuse through membrane 94 and into channel 82 creating a concentration gradient of particles from source region 84 to output 82a thereof over a predetermined time period. As the diffusing particles leave channel 26, the concentration of particles in the portion of sink region 86 adjacent to channel 82 becomes non-zero and the rate at which the particles leave channel 82 changes slightly over time. However, as heretofore described with respect to microfluidic device 10, comparison between the model and experimental data suggests that the approximation of zero sink concentration is valid because the small concentration of incoming particles is diluted by the large fluid volume of sink region 86. One way to mimic an ideal sink would be to periodically flush out, replace or mix the reservoir volume. It is contemplated to add cells to channel 82 during or after the gradient stabilization in order to determine the effects of the gradient on the cells. The cells may be introduced through access port 110 in cell-addition member 93 of microfluidic device 10.

Figure 6:
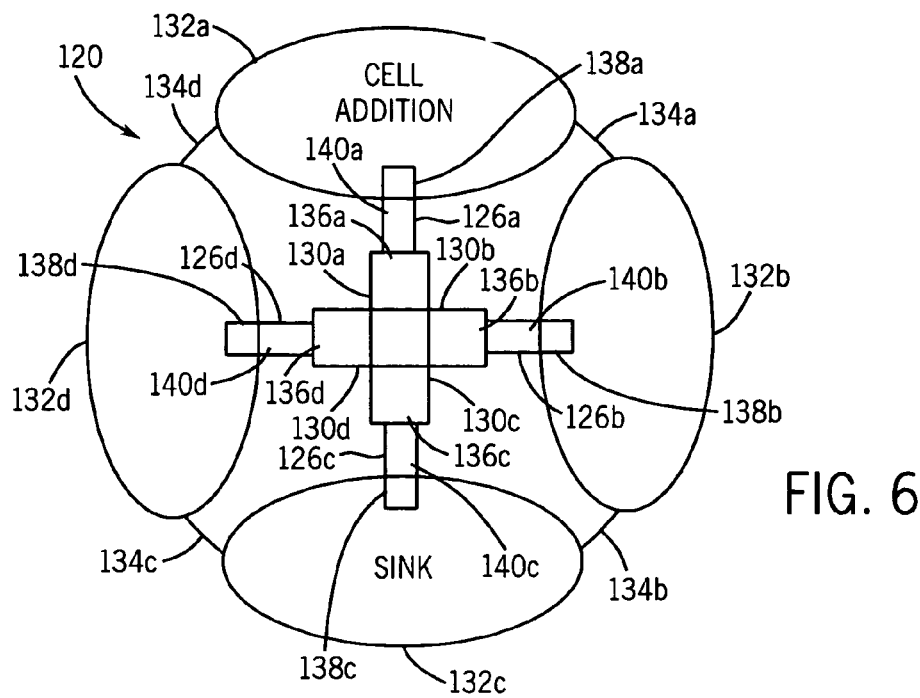
FIG. 6 is a schematic, top plan view of a fourth embodiment of a microfluidic device in accordance with the present invention.

Referring to FIG. 6, a still further embodiment of a microfluidic device in accordance with the present invention is generally designated by the reference numeral 120. Microfluidic device 120 includes a plurality of circumferentially-spaced, channels 126a-126d. Each channel 126a-126d extends along a corresponding longitudinal axis between a corresponding source region 130a-130d and a corresponding enlarged sink region 132a-132d. Sink regions 132a and 132b are interconnected by channel 134a; sink regions 132b and 132c are interconnected by channel 134b; sink regions 132c and 132d are interconnected by channel 134c; and sink regions 132d and 132a are interconnected by channel 134d. Access ports 136a-136d are punched in the upper surface of microfluidic device 120 and communicate with corresponding source regions 130a-130d, respectively. Similarly, cell-addition ports 138a-138d are punched in the upper surface of microfluidic device 120 and communicate with corresponding sink regions 132a-132d, respectively. For reasons heretofore described, sink regions 132a-132d have diameters greater than the corresponding diameters of source regions 130a-130d, respectively. Membranes 140a-140d are positioned in corresponding access ports 136a-136d, respectively.

In operation, access ports 136a-136d; cell-addition ports 138a-138d; channels 126a-126d; channels 134a-134d; source regions 130a-130d; sink regions 132a-132d are filled with a first predetermined solution, such as deionized water. Predetermined fluids having known concentrations of particles, such as cells, molecules, chemical species, organisms or the like therein are introduced or loaded into microfluidic device 120 through access ports 136a-136d. Glass cover slips (not shown) may be placed on the upper surface of the microfluidic device 120 so as to overlap and seal corresponding access ports 136a-136d to prevent evaporation of the predetermined fluids.

As heretofore described, diffusive transport of the predetermined fluids is allowed through membranes 140a-140d while the fluidic resistance of membrane 140a-140d minimize the convective flows in channels 126a-126d, respectively. As a result, the predetermined fluids diffuse through membranes 140a-140d and into corresponding channels 126a-126d, respectively, thereby creating concentration gradients of particles from source regions 132a-132d to corresponding sink regions 132a-132d, respectively over a gradient development period(s). It can be appreciated that the slopes of the concentration gradients in channels 126a-126d may be tuned as heretofore described. Cells, molecules or the like may be introduced into channels 126a-126d through cell-addition ports 138a-138d, respectively, during or after the gradients stabilize in order to determine the effects of the gradients on the introduced cells.

Figure 7:
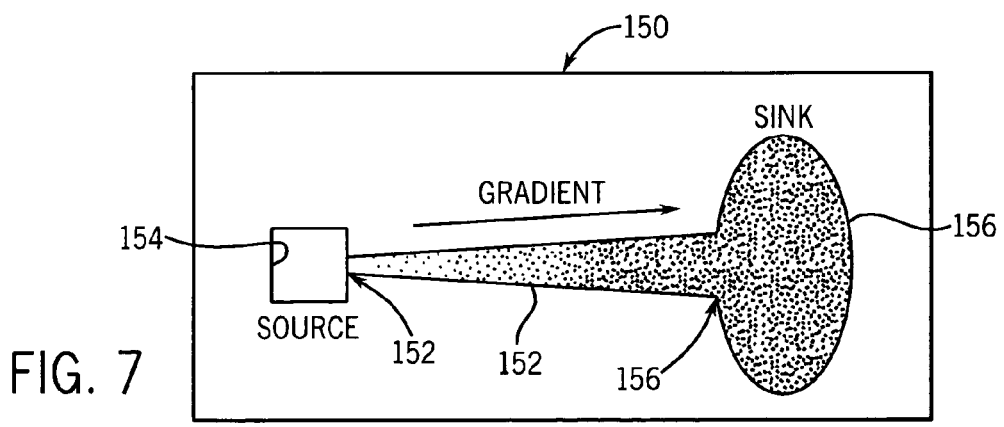
FIG. 7 is a schematic, top plan view of a gradient channel configuration for the microfluidic device of the present invention.

Referring to FIG. 7, a still further embodiment of a microfluidic device in accordance with the present invention is generally designated by the reference numeral 150. Microfluidic device 150 includes channel 152 having first and second ends 152a and 152b, respectively. Channel 152 is generally conical in shape so as to diverge from first end 152a to second end 152b thereof. Channel 152 extends along a longitudinal axis between source region 154 and enlarged sink region 156. An access port (not shown) is punched in the upper surface of microfluidic device 150 and communicates with source region 154. Similarly, a cell-addition port (not shown) is punched in the upper surface of microfluidic device 150 and communicates with sink region 156. For the reasons heretofore described, sink region 156 has a diameter greater than the diameter of source region 154. A membrane (not shown) is positioned in the access port communicating with source region 154.

In operation, the access port, the cell-addition port, channel 152, source region 154, and sink region 156 are filled with a first predetermined solution, such as deionized water. A predetermined fluid having a known concentration of particles, such as cells, molecules, chemical species, organisms or the like, therein are introduced or loaded into microfluidic device 10 through the access port. A glass cover slip (not shown) may be placed on the upper surface of the microfluidic device 150 so as to overlap and seal the access port to prevent evaporation of the predetermined fluid.

Figure 8:
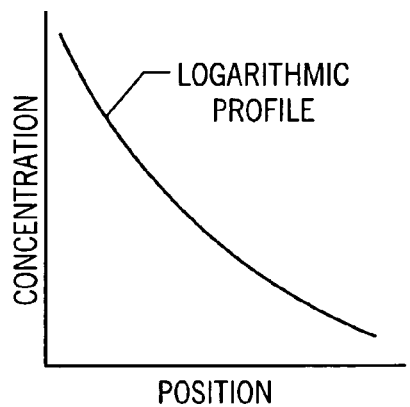
FIG. 8 is a graphical representation of the concentration gradients in the gradient channel of the microfluidic device of FIG. 7 versus the position along the gradient channel.

As heretofore described, diffusive transport of the predetermined fluid is allowed through the membrane while the fluidic resistance of the membrane minimizes the convective flows in channel 152, respectively. As a result, the predetermined fluid diffuses through the membrane and into channel 152 thereby creating a concentration gradient of particles from source region 154 to corresponding sink region 156 over a gradient development period. It can be appreciated that by changing the cross-sectional configuration and/or the shape of channel 152, the slope of the concentration gradient in channel 152 is changed. By way of example, the tapered geometry of channel 152 yields a steady state, concentration gradient having a logarithmic profile, FIG. 8. Cells, molecules or the like may be introduced into channel 152 through the cell-addition port during or after the gradient stabilization has occurred in order to determine the effects of the gradient on the introduced cells. By providing channel 152 with a generally conical configuration, the linear density of the cells in channel 152 may be increased, thereby allowing a user to study the effects thereof. Other configurations of channel 152 are contemplated as being within the scope of the present invention.

Various modes of carrying out the invention are contemplated as being within the scope of the following claims particularly pointing out and distinctly claiming the subject matter that is regarded as the invention.

We claim:

1. A microfluidic device for generating a gradient, comprising:
    a body defining;
        a source;
        a gradient channel having an input port and an output; and
        a sink communicating with the output of the gradient channel;
    a first membrane separating the input port of the gradient channel and the source;
    an access port extending through the body and communicating with the gradient channel;
    a second membrane extending across the access port and being downstream of the input port of the gradient channel.

2. The microfluidic device of claim 1 further wherein the sink includes a flow channel extending through the body.

3. The microfluidic device of claim 1 wherein the sink includes a chamber having a predetermined volume.

4. The microfluidic device of claim 1 wherein the gradient channel has a predetermined volume and wherein the predetermined volume of the chamber of the sink is greater than the predetermined volume of the gradient channel.

5. The microfluidic device of claim 3 wherein the access port communicates with the gradient channel through the sink.

6. A microfluidic device for generating a gradient, comprising:
    a body having:
        a source channel extending along a first axis and having an output;
        a gradient channel at a predetermined angle to the source channel,
        the gradient channel including an input communicating with the output of the source channel and an output;
        a sink communicating with the output of the gradient channel, the sink including a flow channel extending through the body; and
        a media addition port communicating with the gradient channel;
    a first membrane extending through the source channel; and
    a second membrane disposed across the media addition port.

7. The microfluidic device of claim 6 wherein the gradient channel extends along a second axis that is generally perpendicular to the first axis.

8. The microfluidic device of claim 6 wherein gradient channel has a predetermined volume and wherein the predetermined volume of the sink is greater than the predetermined volume of the gradient channel.

9. The microfluidic device of claim 6 wherein the media addition port communicates with the gradient channel through the sink.

10. The microfluidic device of claim 6 wherein the first membrane is formed from a pourous material.

11. The microfluidic device of claim 6 wherein the source channel has an input operatively connect to a source of particles, the input of the source channel lying in a first plane and the gradient channel lying in a second plane axially spaced from the first plane.

12. The microfluidic device of claim 6 wherein the channel diverges from the input to the output.

* * * * *